(12) United States Patent
Brathe et al.

(10) Patent No.: US 8,633,337 B2
(45) Date of Patent: Jan. 21, 2014

(54) METHOD AND SYNTHESIS

(75) Inventors: Anders Brathe, Sandefjord (NO); Andreas Olsson, Oslo (NO); Mikkel Thaning, Oslo (NO); Steffen Bugge, Oslo (NO)

(73) Assignee: GE Healthcare Limited, Little Chalfont (GB)

( * ) Notice: Subject to any disclaimer, the term of this patent is extended or adjusted under 35 U.S.C. 154(b) by 0 days.

(21) Appl. No.: 13/696,960

(22) PCT Filed: May 13, 2011

(86) PCT No.: PCT/EP2011/057757
§ 371 (c)(1),
(2), (4) Date: Nov. 8, 2012

(87) PCT Pub. No.: WO2011/141568
PCT Pub. Date: Nov. 17, 2011

(65) Prior Publication Data
US 2013/0060064 A1    Mar. 7, 2013

Related U.S. Application Data

(60) Provisional application No. 61/334,599, filed on May 14, 2010.

(30) Foreign Application Priority Data

May 14, 2010    (GB) .................................. 1008047.1

(51) Int. Cl.
*C07C 277/08*    (2006.01)
*B01J 19/00*    (2006.01)

(52) U.S. Cl.
USPC .......... 564/238; 422/159; 424/1.37; 424/1.89

(58) Field of Classification Search
CPC ...................................................... C07C 227/08
USPC .................. 422/159; 424/1.37, 1.89; 564/238
See application file for complete search history.

(56) References Cited

U.S. PATENT DOCUMENTS 6,774,263 B1    8/2004    Durant et al.
8,058,311 B2 *    11/2011    Robins et al. ................. 514/634

FOREIGN PATENT DOCUMENTS

| WO | 98/04131 | 2/1998 |
| WO | 99/02145 | 1/1999 |
| WO | 99/18962 | 4/1999 |
| WO | 2004/007440 | 1/2004 |
| WO | 2006/136846 | 12/2006 |

OTHER PUBLICATIONS

GB1008047.1 Search Report Dated Aug. 25, 2010.
PCT/EP2011/057757 ISRWO Dated Aug. 24, 2011.
Robins Bioorganic & Medicinal Chemistry Letters, vol. 20 No. 5., Jan. 20, 2010.

* cited by examiner

*Primary Examiner* — Yong Chu

(57) ABSTRACT

The present invention provides a method for the preparation of a radiolabeled guanidine derivative, in particular wherein the radiolabeled guanidine derivative is a positron emission tomography (PET) tracer. Certain intermediates useful in said method are also provided, as well as means for carrying out said method in an automated fashion. The method of the invention provides advantages over known methods for the preparation of radiolabeled guanidine derivatives.

14 Claims, No Drawings

METHOD AND SYNTHESIS

This application is a filing under 35 U.S.C. 371 of international application number PCT/EP2011/057757, filed May 13, 2011, which claims priority to U.S. application No. 61/334,599 filed May 14, 2010 and Great Britain application number 1008047.1 filed May 14, 2010, the entire disclosure of which is hereby incorporated by reference.

TECHNICAL FIELD OF THE INVENTION

The present invention resides in the field of chemical synthesis. More specifically, the present invention relates to novel methods useful in the synthesis of a positron emission tomography (PET) tracer, and novel intermediates useful in said method.

DESCRIPTION OF RELATED ART

WO 94/27591 describes certain substituted guanidines and their use for treatment and/or prophylaxis of neurological conditions such as epilepsy, neurodegenerative conditions and/or nerve cell death resulting from e.g. hypoxia, hypoglycemia, brain or spinal chord ischemia, brain or spinal chord trauma. WO 94/27591 describes that the substituted guanidines can be prepared by the reaction of an amine, typically an amine salt such as an amine hydrochloride, with a preformed alkyl or aryl cyanamide (Safer et al 1948 J Org Chem; 13: 924) or the corresponding N-substituted alkyl or aryl cyanamide.

WO 2004/007440 and WO 2006/136846 describe radiolabeled guanidine derivatives and their use for imaging central nervous system (CNS) receptors and teach synthesis of these radiolabeled derivatives from precursor compounds. For example, WO 2006/136846 teaches a compound of Formula (A):

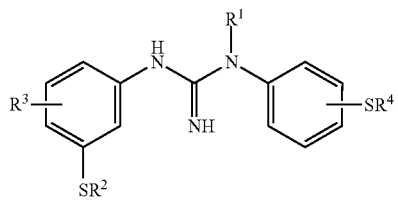

(A)

or a salt or solvate thereof, wherein:
$R^1$ is hydrogen or $C_{1-4}$ alkyl;
$R^2$ and $R^4$ are each independently selected from $C_{1-4}$ alkyl, [$^{11}$C]—$C_{1-4}$alkyl, and [$^{18}$F]—$C_{1-4}$ fluoroalkyl provided that at least one of $R^2$ and $R^4$ is [$^{11}$C]—$C_{1-4}$alkyl or [$^{18}$F ]—$C_{1-4}$ fluoroalkyl, and,
$R^3$ is halo.

WO 2006/136846 teaches that the above compound of Formula (A) is synthesized by reaction of a suitable source of $^{11}$C or $^{18}$F with a precursor compound of Formula (B):

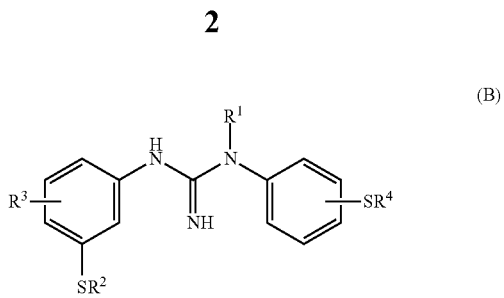

(B)

wherein one of $R^2$ or $R^4$ is hydrogen, and the other is hydrogen, $C_{1-4}$ alkyl, or a thiol protecting group such as benzyl; $R^1$ is hydrogen or $C_{1-4}$alkyl, and $R^3$ is halo.

WO 2006/136846 also teaches that the method to obtain the precursor compound of Formula (B) above wherein $R^2$ is hydrogen is based on that disclosed by Hu et al (J. Med. Chem. 1997; 40(26): 4281-9), wherein a compound of Formula (C):

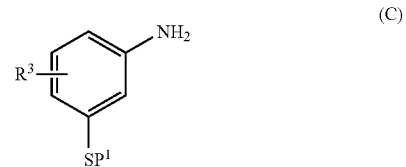

(C)

or a salt or solvate thereof, wherein $R^3$ is halo and $P^1$ is a thiol protecting group;
is reacted with a compound of Formula (D):

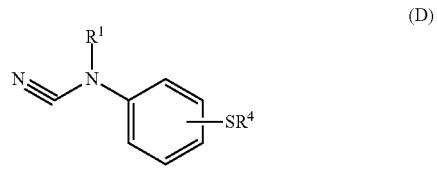

(D)

wherein $R^1$ is hydrogen or $C_{1-4}$ alkyl and $R^4$ is as defined for the desired compound of Formula (B).

This method has also been recently reported by Robins et al (2010 Bioorg Med Chem Lett; 20: 1749-51) as a successful way to obtain the following $^{18}$F-labelled S-fluoroalkyl diarylguanidines:

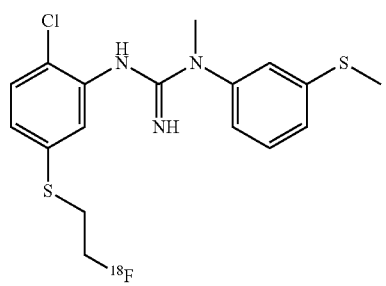

-continued

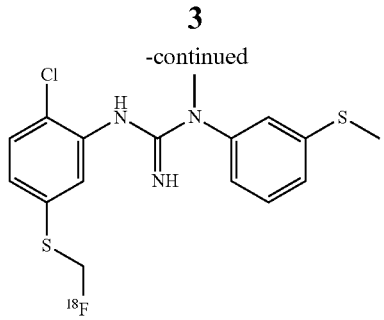

However, the above-described method of preparing the radiolabeling precursor of Formula (B) suffers from a number of problems. First of all, tin chloride is used in a reduction step used in the preparation of the compound of Formula (C) from sulfonylchloride starting material. Residual tin complicates the workup by gel forming tin hydroxides at pH>2. Furthermore, following this reduction step, a benzyl protective group is introduced at the thiol and this group has to be removed at the end of the synthesis, requiring use of $AlCl_3$ followed by flash chromatography. There is therefore a need for a method to prepare this radiolabeling precursor that overcomes these problems.

In addition, and not described in the prior art, the present inventors have found that the compound of Formula (B) wherein $R^2$ is hydrogen decomposes to form a disulfide impurity, even under what would be considered "inert" conditions, which complicates subsequent radiolabeling to obtain the corresponding compound of Formula (A). There is therefore an additional need for alternative strategies to obtain said compound of Formula (A) that do not suffer from this disadvantage.

SUMMARY OF THE INVENTION

The present invention provides a method to prepare a radiolabeled guanidine derivative. A novel intermediate and it's method of synthesis are also provided. In the method of the invention, use of a step comprising iodine oxidation has the advantage that the iodine oxidizes any tin present as a consequence of the initial tin chloride reduction step. No protecting groups are required in the method of the invention, thereby eliminating the need for a deprotection step. In addition, the method of the invention overcomes the problem observed by the present inventors with formation of a disulphide impurity. The method of the invention therefore overcomes a number of problems associated with known methods for the preparation of radiolabeled guanidine derivatives.

DETAILED DESCRIPTION OF THE INVENTION

In one aspect, the present invention provides a method to obtain a positron emission tomography (PET) tracer of Formula I:

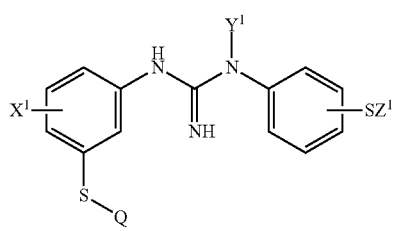

(I)

wherein:
$X^1$ is an X group selected from $C_{1-4}$ alkyl or halo;
$Y^1$ is a Y group selected from hydrogen or $C_{1-4}$ alkyl;
$Z^1$ is a Z group which is $C_{1-4}$ alkyl; and,
Q is [$^{11}C$]$C_{1-4}$ alkyl- or [$^{18}F$]—$C_{1-4}$fluoroalkyl-;
wherein said method comprises:
(a) providing a compound of Formula II:

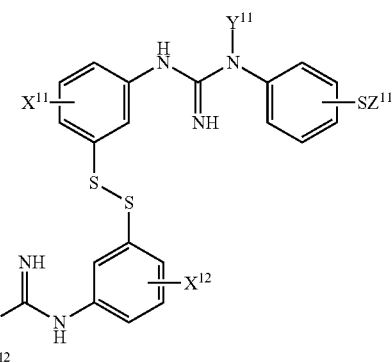

(II)

wherein:
$X^{11}$ and $X^{12}$ are the same and are both an X group as defined for $X^1$;
$Y^{11}$ and $Y^{12}$ are the same and are both a Y group as defined for $Y^1$, and,
$Z^{11}$ and $Z^{12}$ are the same and are both a Z group as defined for $Z^1$,
(b) reducing said compound of Formula II with a reducing agent to obtain a compound of Formula III:

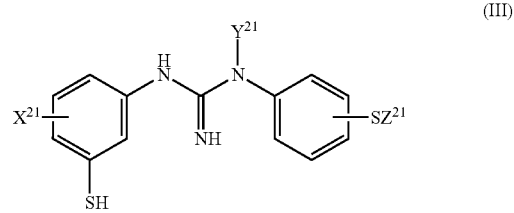

(III)

$X^{21}$ is an X group as defined for $X^1$;
$Y^{21}$ is a Y group as defined for $Y^1$; and,
$Z^{21}$ is a Z group as defined for $Z^1$;
(c) reacting the compound of Formula III as obtained in step (b), with either [$^{11}C$]$C_{1-4}$ alkyl-$LG^1$ or [$^{18}F$]—$C_{1-4}$ fluoroalkyl-$LG^2$, wherein $LG^1$ and $LG^2$ are independently halo, or the group —O—$SO_2$—$R^1$ wherein $R^1$ represents an optionally-substituted $C_{6-10}$ aryl, an optionally-substituted $C_{1-4}$ alkyl, or $C_{1-4}$ fluoroalkyl, wherein said reacting is carried out in a suitable solvent.

The term "PET tracer" refers to a chemical compound that comprises a radionuclide that undergoes positron emission decay (also known as positive beta decay), and is therefore detectable using PET imaging. The most commonly used radionuclides for PET are $^{18}F$ and $^{11}C$.

The term "alkyl", alone or in combination, means a straight-chain or branched-chain alkyl radical having the general formula $C_nH_{2n+1}$. Examples of such radicals include methyl, ethyl, and isopropyl.

The term "halogen" or "halo" in the context of the present invention means a substituent selected from fluorine, chlorine, bromine or iodine.

The term "reducing agent" (also commonly referred to as a "reductant" or "reducer") is the element in an oxidation-reduction reaction that donates an electron to another species. For the present invention, non-limiting examples of suitable reducing agents for use in step (b) in the above-defined method include: sodium borohydride (NaBH$_4$), zinc in hydrochloric acid, zinc in acetic acid, magnesium in hydrochloric acid, sodium hydrogentelluride (NaTeH) in ethanol, lithium aluminium hydride (LiAlH$_4$) in tetrahydrofuran, indium in ammonium chloride, and sodium hydride (NaH). A preferred reducing agent is NaBH$_4$. In a preferred embodiment, the reducing agent is bound to a solid phase such as a resin in the form of particles such as beads.

The term "fluoroalkyl" refers to an alkyl as defined above that comprises a fluorine atom in place of a hydrogen. Specifically, the term fluoroalkyl as used herein is taken to mean [$^{18}$F]fluoroalkyl, and as such the fluorine atom comprised therein is radioactive $^{18}$F. Preferably, said fluoroalkyl includes a single $^{18}$F atom, most preferably at the terminal end of the chemical group.

The term "leaving group" refers to a moiety suitable for nucleophilic substitution and is a molecular fragment that departs with a pair of electrons in heterolytic bond cleavage.

The term "aryl" refers to a monovalent aromatic hydrocarbon having a single ring (i.e. phenyl) or fused rings (i.e. naphthalene).

A chemical group defined herein as "optionally substituted" may either have no substituents or may include one or more substituents. Preferred substituents include $C_{1-4}$ alkyl, $C_{1-4}$ haloalkyl, halo, and nitro, wherein alkyl is as defined above, "haloalkyl" is an alkyl as defined above that comprises a halo, halo is as defined above, and "nitro" refers to the group —NO$_2$. Accordingly, examples of preferred —O—SO$_2$—R$^1$ groups for the present invention include: toluenesulfonic acid, nitrobenzenesulfonic acid, benzenesulfonic acid, trifluoromethanesulfonic acid, fluorosulfonic acid, and perfluoroalkylsulfonic acid.

The reaction step (c) with [$^{11}$C]C$_{1-4}$ alkyl-LG$^1$ or [$^{18}$F]—C$_{1-4}$ fluoroalkyl-LG$^2$ is an alkylation reaction carried out in a suitable solvent. A "suitable solvent" is one in which the reactants are readily soluble and readily react to result in the desired product. Such a suitable solvent may be selected from the group comprising N,N-dimethylformamide (DMF), acetone, dichloromethane (DCM), chloroform, dimethylsulphoxide (DMS), methanol, ethanol, propanol, isopropanol, tetrahydrofuran (THF), or acetonitrile.

In a preferred embodiment of the method of the invention said compound of Formula II is a compound of Formula IIa:

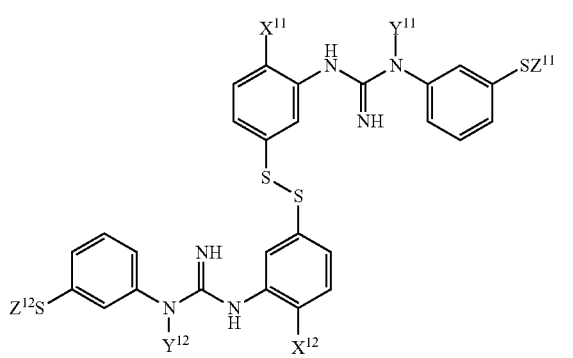

(IIa)

wherein:

X$^{11}$ and X$^{12}$ are the same and are both an X group as suitably and preferably defined herein.

Y$^{11}$ and Y$^{12}$ are the same and are both a Y group as suitably and preferably defined herein; and, Z$^{11}$ and Z$^{12}$ are the same and are both a Z group as suitably and preferably defined herein.

Preferably for the method of the invention said X group is halo, most preferably chloro.

Preferably for the method of the invention said Y group is $C_{1-4}$ alkyl, most preferably methyl.

Preferably for the method of the invention said Z group is methyl.

In a preferred embodiment for the intermediates and the product of the method of the invention, said X group is chloro, said Y group is methyl and said Z group is methyl.

In summary, the compound of Formula II provided in step (a) of the method of the invention is obtained by reacting a compound of Formula IV:

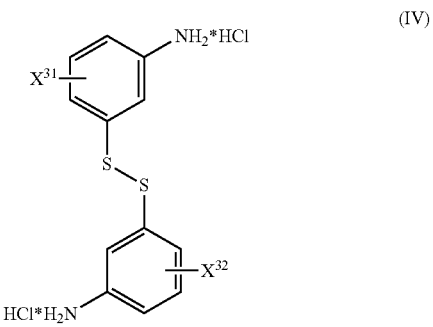

(IV)

wherein X$^{31}$ and X$^{32}$ are the same and are both an X group as suitably and preferably defined herein;

with a compound of Formula V:

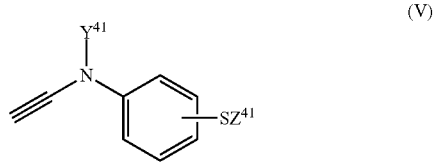

(V)

wherein Y$^{41}$ is a Y group as suitably and preferably defined herein, and Z$^{41}$ is a Z group as suitably and preferably defined herein.

The coupling of the compound of Formula IV with the cyanamide of Formula V may be performed without solvent, or in the presence of a high boiling non-protic solvent such as chlorobenzene, toluene, or xylene. This reaction may be effected at elevated temperature, for example 50 to 200° C., preferably at around 130° C.

The above-defined compound of Formula IV is obtained by iodine oxidation of a compound of Formula VI
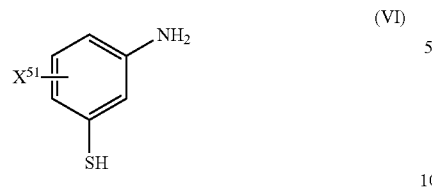
(VI)
wherein $X^{51}$ is an X group as suitably and preferably defined herein.
Table 1 below illustrates a known method to obtain a compound of Formula III alongside the methods used in the present invention:
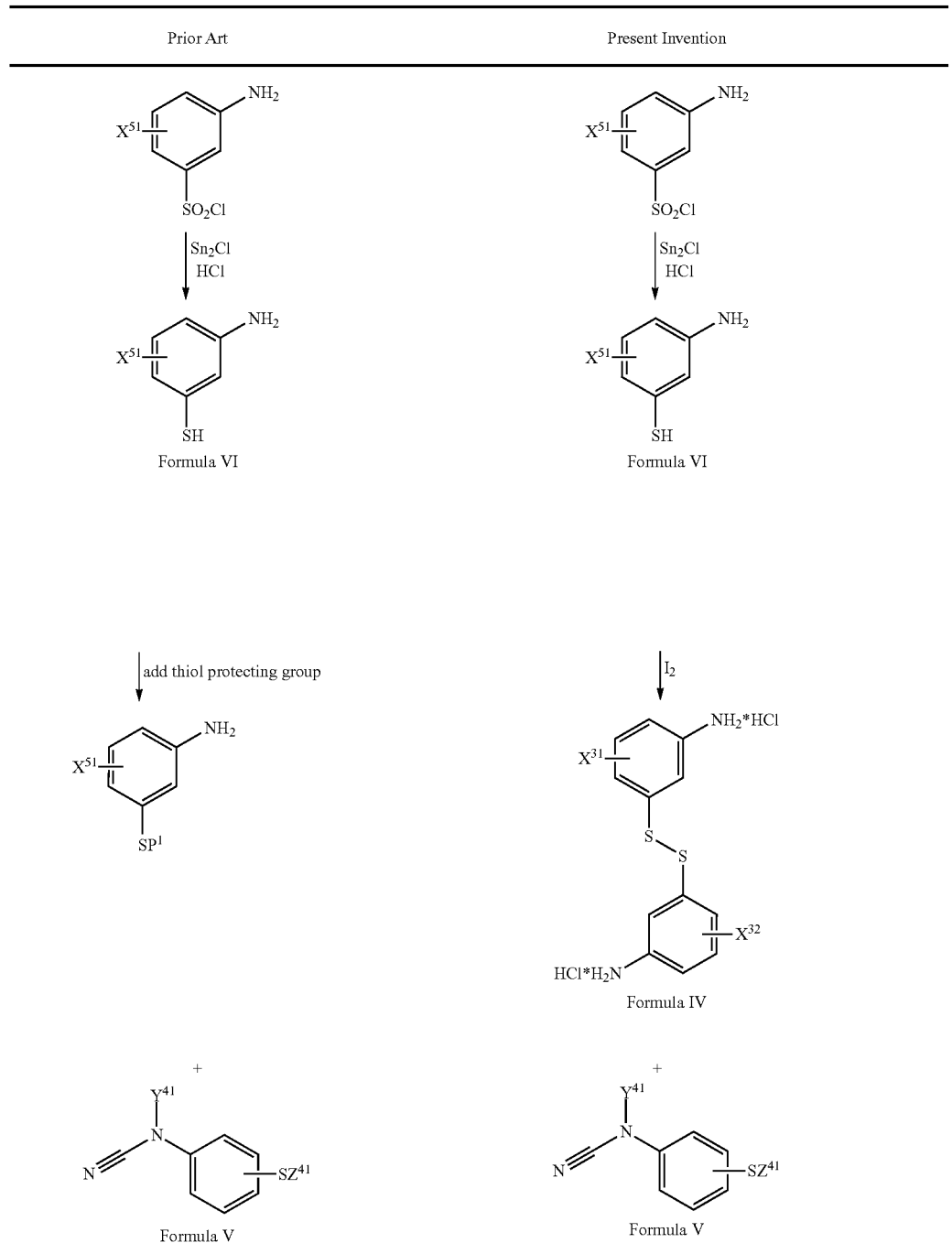

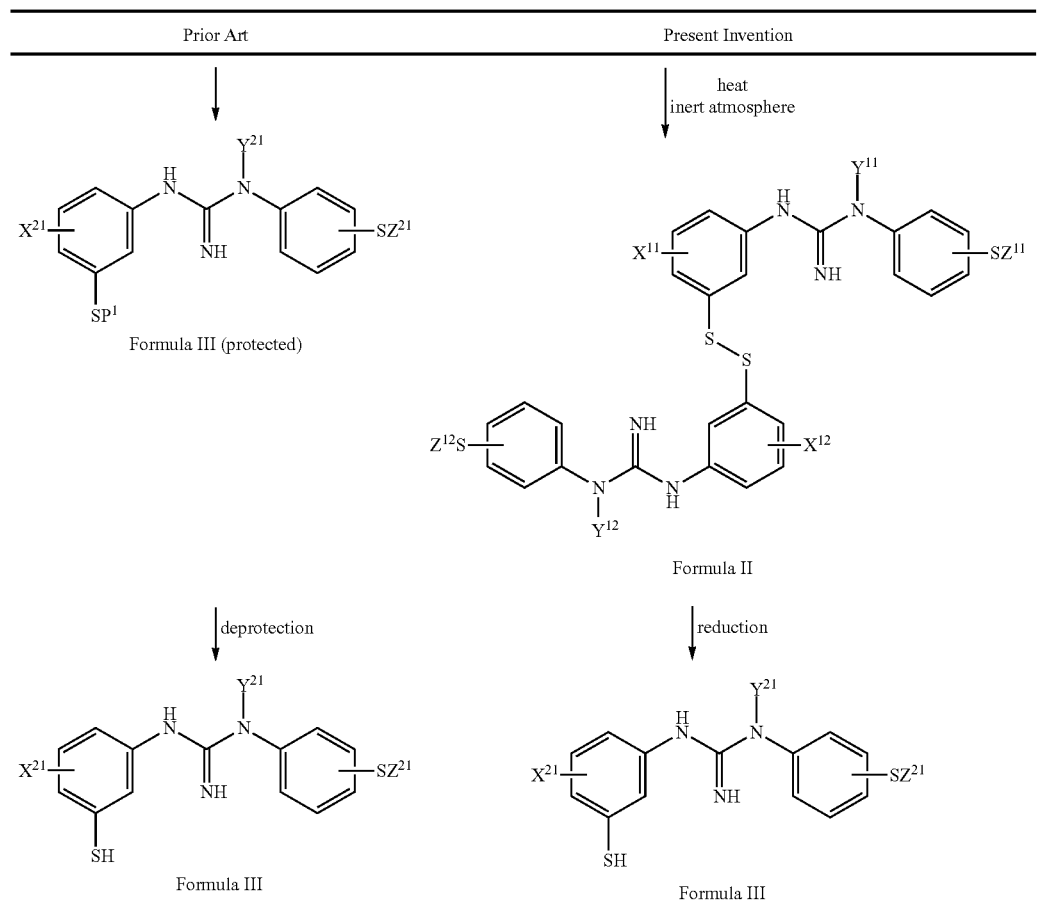

In Table 1:
each X, Y and Z group is as suitably and preferably defined herein for X, Y and Z, respectively; and,
$P^1$ is a thiol protecting group.

Protecting groups are well known to those skilled in the art. For thiol groups suitable protecting groups are benzyl, trityl, and 4-methoxybenzyl. The use of further protecting groups are described in 'Protective Groups in Organic Synthesis', Theorodora W. Greene and Peter G. M. Wuts, (Fourth Edition, John Wiley & Sons, 2007).

The cyanamide starting material of Formula V in Table 1 can be prepared according to the method described by Hu et al (1997 J Med Chem; 40: 4281-4289), by reaction of cyanogen bromide with the primary amine in diethyl ether, or by alkylation of an arylcyanamide with sodium hydride or alkyl halide in tetrahydrofuran. The nitrobenzenesulfonyl chloride starting material illustrated in Table 1 is commercially available. The first step in Table 1, common to the prior art method and the method of the present invention, is reduction of the nitrobenzenesulfonyl chloride starting material to form the aminobenzenethiol intermediate of Formula VI. In the second step of the prior art method, a protecting group is placed onto the thiol group, which is removed at the end of the synthesis using known methods. For example, where the thiol protecting group is benzene, $AlCl_3$ and flash chromatography may be used for its removal. The disulfide of Formula IV is obtained in the method of the invention by iodine oxidation of the aminobenzenethiol intermediate of Formula VI. This step has the advantage that the iodine additionally oxidizes any tin present. In the prior art method, residual tin complicates the workup because the tin hydroxides form gels at pH>2. The method used in the present invention overcomes this problem as oxidised tin does not form gels, thereby facilitating extractive work up of the product. The method is furthermore advantageous because use of the disulfide intermediate of Formula IV circumvents the need to protect the thiol group. The method used in the present invention to obtain a compound of Formula III illustrated in Table I above may be regarded as another aspect of the present invention.

The present inventors have observed that the compound of Formula III decomposes to form the disulfide of Formula II, even under what would be considered "inert" conditions. This problem is effectively overcome by storage of the disulfide compound of Formula II instead of the compound of Formula III. In the method to obtain a PET tracer of Formula I the compound of Formula II is reduced by step (b) immediately before the radiolabeling step (c). In order to facilitate this, steps (b) and (c) are preferably carried out in the same vessel. A further advantage of this strategy over the prior art methods is that it is not necessary to include a base in the reaction step (c). Inclusion of a base in the reaction is required by the methods taught by the prior art to deprotonate the thiol in order to allow reaction with the radiolabeled synthon. Suitable bases taught in the prior art methods include inorganic bases such as potassium carbonate, potassium hydroxide, or sodium hydride, or organic bases such as a trialkylamine, for example triethylamine, diisopropylethylamine, or dimethylaminopyridine. In the method of the present invention, once the compound of Formula II is reduced in step (b) it can be reacted directly in step (c) with [$^{11}$C]C$_{1-4}$ alkyl-LG$^1$ or [$^{18}$F]—C$_{1-4}$ fluoroalkyl-LG$^2$ to obtain the PET tracer of Formula I without any requirement to add a base.

[$^{11}$C]C$_{1-4}$ alkyl-LG$^1$ provided in step (c) of the method can be prepared using methods well-known in the art of radiochemistry. For example, [$^{11}$C]methyl iodide can be prepared by reduction of [$^{11}$C]carbon dioxide with lithium aluminium hydride followed by reaction with hydroiodic acid. [$^{11}$C] carbon dioxide is usually produced by the $^{14}$N(p,α)$^{11}$C reaction from nitrogen gas containing trace amounts of oxygen. [$^{11}$C]methyl triflate can be prepared from [$^{11}$C]methyl iodide, or by gas phase reaction of [$^{11}$C]methyl bromide preprared from [$^{11}$C]methane. All these methods are described in more detail in "Aspects on the Synthesis of $^{11}$C-Labeled Compounds", Chapter 3 of Handbook of Radiopharmaceuticals (2003 Welch & Redvanly eds. pp 141-194). A preferred [$^{11}$C] C$_{1-4}$ alkyl-LG$^1$ is selected from [$^{11}$C]methyl-LG$^1$ or [$^{11}$C]ethyl-LG$^1$, and LG$^1$ is preferably iodo.

[$^{18}$F]—C$_{1-4}$ fluoroalkyl-LG$^2$ provided in step (c) of the method can be prepared by radiolabeling alkyldihalides or sulfonates using [$^{18}$F]fluoride. [$^{18}$F]Fluoride is typically obtained as an aqueous solution which is a product of the irradiation of an [$^{18}$O]-water target. It has been widespread practice to carry out various steps in order to convert [$^{18}$F] Fluoride into a reactive nucleophilic reagent, such that it is suitable for use in nucleophilic radiolabeling reactions. These steps include the elimination of water from [$^{18}$F]-fluoride ion and the provision of a suitable counterion (Handbook of Radiopharmaceuticals 2003 Welch & Redvanly eds. ch. 6 pp 195-227). Suitable counterions include large but soft metal ions such as rubidium or caesium, potassium complexed with a cryptand such as Kryptofix™, or tetraalkylammonium salts. A preferred [$^{18}$F]—C$_{1-4}$ fluoroalkyl-LG$^2$ is [$^{18}$F]-fluoroethyl-LG$^2$ wherein LG$^2$ is preferably a sulfonate, most preferably tosylate.

Preferably for the method to obtain said PET tracer of Formula I, the reducing step (b) and the reacting step (c) are carried out in immediate sequence. The term "in immediate sequence" should be understood to mean that the reacting step (c) is carried out as soon as possible, i.e. directly, after the reducing step (b), such that there is as little time as practically possible between the two steps and ideally no time between the two steps. In this way, any decomposition of the compound of Formula III to form the disulfide is minimised, thereby facilitating the radiolabeling reaction.

In a particularly preferred embodiment, the above-described method to obtain said PET tracer of Formula I is automated. PET tracers, and [$^{18}$F]-tracers in particular, are now often conveniently prepared on an automated radiosynthesis apparatus. There are several commercially-available examples of such apparatus, including Tracerlab™ and Fastlab™ (both from GE Healthcare Ltd). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. The present invention therefore provides in another aspect a cassette for carrying out these steps wherein said cassette comprises:

(i) a vessel containing the compound of Formula II as suitably and preferably defined herein;
(ii) means for reacting said compound of Formula II with a reducing agent to form a compound of Formula wherein said reducing agent and said compound of Formula III are as suitably and preferably defined herein; and,
(iii) means for reacting said compound of Formula III with either [$^{11}$C]C$_{1-4}$ alkyl-LG$^1$ or [$^{18}$F]—C$_{1-4}$ fluoroalkyl-LG$^2$ to obtain a PET tracer of Formula I, wherein LG$^1$, LG$^2$ and said PET tracer of Formula I are as suitably and preferably defined herein.

The means for reacting said compound of Formula II with said reducing agent may be a vessel containing the reducing agent in solution (or in a soluble) form, wherein the reducing agent is passed through the vessel containing the compound of Formula II in order to effect the reduction. Alternatively, said means may be a vessel in which the reducing agent is bound to a solid phase, wherein the compound of Formula II is passed through the vessel containing the reducing agent in order to effect the reduction. The suitable and preferred embodiments described herein for the reduction step (b) and the reaction step (c) also apply to the method as carried out on the cassette of the invention.

The cassette may additionally comprise:

an ion-exchange cartridge for removal of excess [$^{11}$C]C$_{1-4}$ alkyl-LG$^1$ or [$^{18}$F]—C$_{1-4}$ fluoroalkyl-LG$^2$.

The PET tracer of Formula I obtained by the method of the invention is useful as a radioligand for the NMDA receptor and can be used in an in vivo diagnostic or imaging method such as positron emission tomography (PET). A PET tracer of Formula I as defined above, or a salt or solvate thereof, may be used to image the NMDA receptor in healthy human volunteers. Because the PET tracer of Formula I is useful for in vivo imaging of NMDA receptors it thus also has utility in the diagnosis of NMDA-mediated disorders, such as stroke, brain or spinal chord trauma, epilepsy, Alzheimer's disease, or Huntington's disease.

BRIEF DESCRIPTION OF THE EXAMPLES

Example 1 describes the synthesis of 1,1'-(5,5'-disulfanediylbis(2-chloro-5,1-phenylene))bis(3-methyl-3-(3-(methylthio)phenyl)guanidine).

Example 2 describes the synthesis of 3-(2-chloro-5-mercaptophenyl)-1-methyl-1-(3-(methylthio)phenyl)guanidine.

Example 3 describes the synthesis of 3-(2-chloro-5-((2-fluoroethyl)thio)phenyl)-1-methyl-1-(3-(methylthio)phenyl) guanidine.

Example 4 describes the synthesis of 3-(2-chloro-5-((2-fluoroethyl)thio)phenyl)-1-methyl-1-(3-(methylthio)phenyl) guanidine using resinbound borohydride.

LIST OF ABBREVIATIONS USED IN THE EXAMPLES

DCM dichloromethane
EtOH ethanol
g gram(s)
HPLC high performance liquid chromatography
M molar
MeOH methanol
mg milligram(s)
mL millilitre(s)
mmol millimole(s)
NMR nuclear magnetic resonance
RT room temperature

EXAMPLES

Unless otherwise specified, the intermediates and reagents used in the examples were purchased from Sigma Aldrich, Merck, or Alfa Aesar.

Example 1

Synthesis of 1,1'-(5,5'-disulfanediylbis(2-chloro-5,1-phenylene))bis(3-methyl-3-(3-(methylthio)phenyl) quanidine)

1(a) Synthesis of 5,5'-disulfanediylbis(2-chlorobenzenaminium)chloride

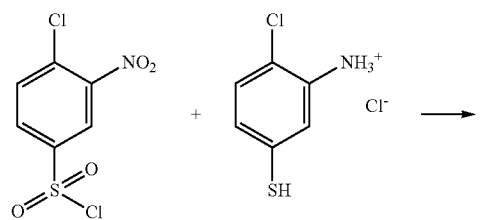

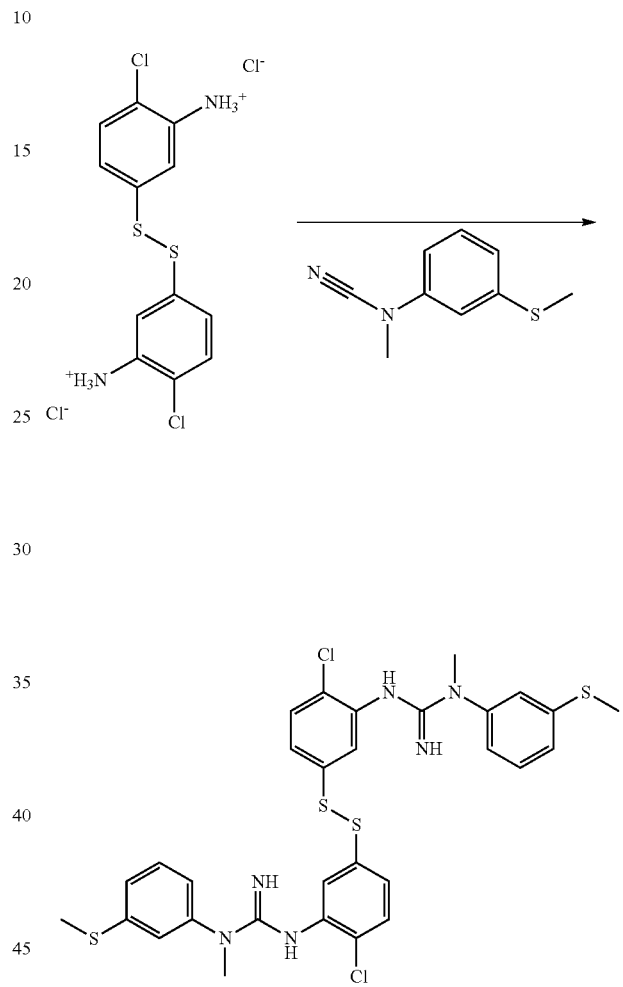

Tin(II)chloride (33.32 g, 175.74 mmol) was dissolved in 30% hydrochloric acid (99.7 mL) and 4-chloro-3-nitrobenzene-1-sulfonyl chloride (5.00 g, 19.553 mmol) was added before submerging the flask in a 125° C. preheated oil bath. After 3 hours all solid material had dissolved and the reaction mixture was allowed to cool to RT, which caused spontaneous crystallization.

The crystals (contaminated with Tin) were filtered off, dissolved in water (250 mL) and portions of iodine solution (50 mg/mL) were added until HPLC analysis confirmed that all the 2-chloro-5-mercaptobenzenaminium chloride had been converted to 5,5'-disulfanediylbis(2-chlorobenzenaminium)chloride. The solution was filtered, and water (400 mL) was added to the filtrate, followed by stirring and neutralization using NaOH solution (~1 mL, 10%). The solution was extracted with diethyl ether (4×150 mL), dried with magnesium sulphate (anhydrous) and filtered. To the ether solution was added HCl (dry, 1M in diethyl ether, 10 mL), the solution was filtered and the filtrate was dried under vacuum to give 5,5'-disulfanediylbis(2-chlorobenzenaminium)chloride as an off-white powder (21.47 g, 63%).

$^1$H NMR (400 MHz, CDCl$_3$): δ 7.154 (d, J=8.3 Hz, 2H), δ 6.865 (d, J=2.2 Hz, 2H), δ 6.783 (dd, J$_1$=2.2 Hz, J$_2$=8.3 Hz, 2H), δ 4.080 (broad s, 4H)

1(b) Synthesis of 1,1'-(5,5'-disulfanediylbis(2-chloro-5,1-phenylene))bis(3-methyl-3-(3-(methylthio)phenyl)quanidine)

A mixture of 5,5'-disulfanediylbis(2-chlorobenzenaminium) chloride (1.0 g, 2.6 mmol) and N-methyl-N-(3-(methylthio)phenyl)cyanamide (1.83 g, 10.3 mmol) was heated to 130° C. This thick slow-stirring melt was left for 17 h (HPLC yield after 1 hour ~80%), then allowed to cool to RT. The solid was dissolved in DCM (25 mL), extracted with water (3×200 mL) and the combined aqueous phases back-extracted with DCM (50 mL). The aqueous phase was neutralised with NaHCO$_3$ and extracted with diethyl ether (3×150 mL). The combined organic phases were dried with magnesium sulphate (~5 g), filtered and concentrated to dryness under reduced pressure to give 1,1'-(5,5'-disulfanediylbis(2-chloro-5,1-phenylene))bis(3-methyl-3-(3-(methylthio) phenyl)guanidine) (1.16 g, 1.7 mmol, 67%, HPLC purity 94.8%) as off-white powder.

$^1$H NMR (400 MHz, CDCl$_3$): δ 7.300 (t, J=7.9 Hz, 2H), δ 7.298 (d, J=8.3 Hz, 2H), δ 7.175 (t, J=1.9 Hz, 2H), δ 7.122 (ddd, J$_1$=1.0, J$_2$=1.8 Hz, J$_3$=7.9 Hz, 2H), δ 7.108 (d, J=2.3 Hz, 2H), δ 7.054 (ddd, J₁=1.0, J₂=2.2 Hz, J₃=7.9 Hz, 2H), δ 7.049 (dd, J₁=2.3, J₂=8.3 Hz, 2H), δ 3.893 (broad s, 4H), δ 3.338 (s, 6H), δ 2.494 (s, 6H).

Example 2

Synthesis of 3-(2-chloro-5-mercaptophenyl)-1-methyl-1-(3-(methylthio)phenyl)quanidine

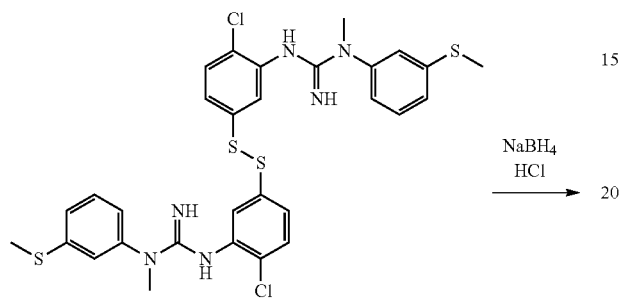

-continued

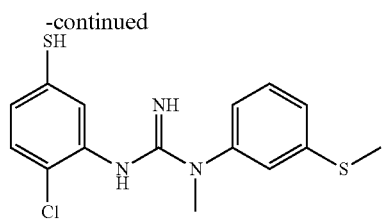

1,1'-(disulfanediylbis(2-chloro-5,1-phenylene))bis(3-methyl-3-(3-(methylthio)phenyl)guanidine) (3.1 g, 4.6 mmol), obtained as described in Example 1, was suspended in EtOH (62 mL) and then sodium borohydride (0.5 g, 13.8 mmol) was added in portions. The reaction solution was left to stir overnight under an inert atmosphere. The reaction was cooled to 10 degrees before quenching with hydrochloric acid in ether (2M) and concentrated to dryness under reduced pressure to give a creamy solid. The solid was purified by column chromatography (CHCl₃->7% MeOH in CHCl₃) to give 3-(2-chloro-5-mercaptophenyl)-1-methyl-1-(3-(methylthio)phenyl)guanidine (2.5 g, 6,7 mmol, 73.6%) as a white foam.

1H NMR (500 MHz, CDCl3). δ 9.686 (s, 1H), δ 8.531 (s,2H), δ 7.132 (t, J=7.8 Hz, 1H), δ 7.032 (d, J=8.4 Hz, 1H), δ 7,022 (d, J=7.8 Hz, 1H), δ 7.014 (s, 1H), δ 6.922 (s, 1H), δ 6.892 (d, J=8.4 Hz, 1H), δ 6.855 (d, J=7.8 Hz, 1H), δ 3.740 (s, 1H), δ 3.656 (s, 3H), δ 2.460 (s, 3H).

Example 3

Synthesis of 3-(2-chloro-5-((2-fluoroethyl)thio)phenyl)-1-methyl-1-(3-(methylthio)phenyl)guanidine

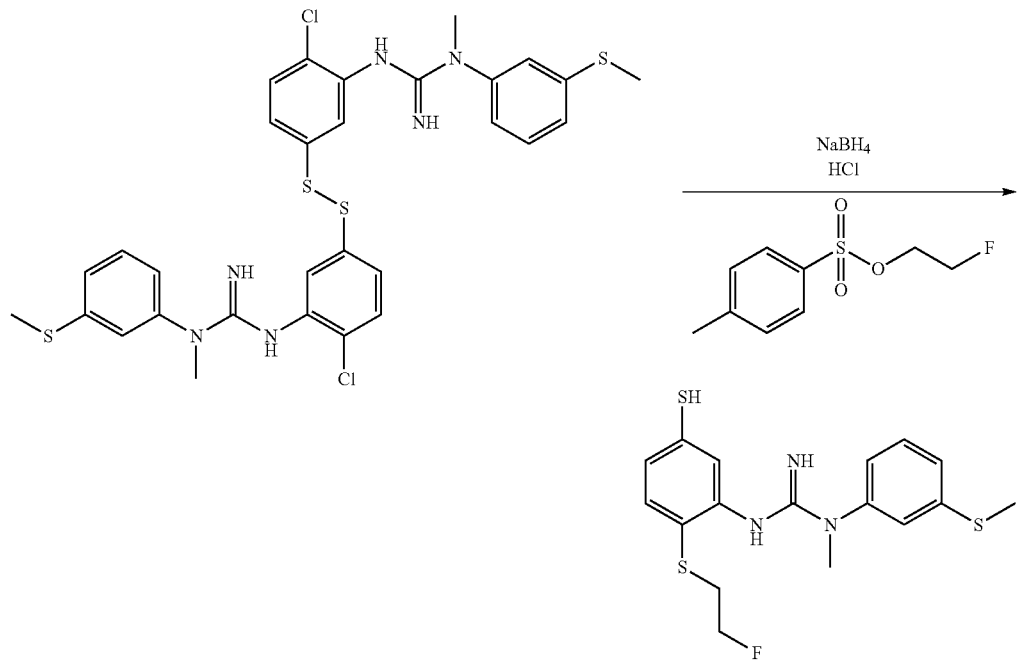

1,1'-(disulfanediylbis(2-chloro-5,1-phenylene))bis(3-methyl-3-(3-(methylthio)phenyl)guanidine) (3.0 g, 4.45 mmol), obtained as described in Example 1, was a dissolved in ethanol (120 mL) and 2-fluoroethyl 4-methylbenzenesulfonate (2.1 g, 9.8 mmol) was added. The clear solution was heated to 60° C. under inert atmosphere and sodium borohydride (0.8 g, 22.3 mmol) was added in portions. The reaction was heated for 45 minutes before being concentrated to dryness under reduced pressure. The crude was purified by column chromatography (CHCl₃->2%, MeOH in CHCl₃) to give 3-(2-chloro-5-((2-fluoroethyl)thio)phenyl)-1-methyl-1-(3-(methylthio)phenyl)guanidine (2.2 g, 5.6 mmol, 62.9%) as a dear slowly crystallizing oil.

¹H NMR (400 MHz, CDCl₃): δ7.28-7.35 (m, 2H), δ7.05-7.25 (m, 4H), δ6.90-6.95 (dd, J₁=3.18 Hz, J₂=8.33 Hz 1H), δ4.6 (t, J=6.75 Hz, 1H), δ4.5 (t, J=6.75 Hz, 1H), δ3.9 (broad S, 1H), δ3.4 (s, 3H), δ3.2(t, J=6.75 Hz, 1H), δ3.15 (t, J=6.75 Hz, 1H), δ2.52 (S, 3H)δ1.65 (broad S, 1H).

Example 4

Synthesis of 3-(2-chloro-5-((2-fluoroethyl)thio)phenyl)-1-methyl-1-(3-(methylthio)phenyl)quanidine Using Resinbound Borohydride

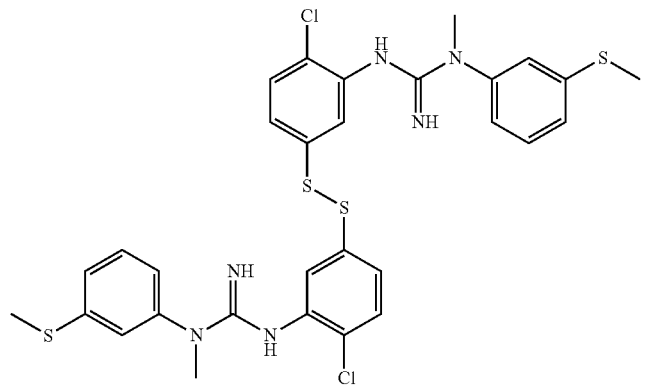

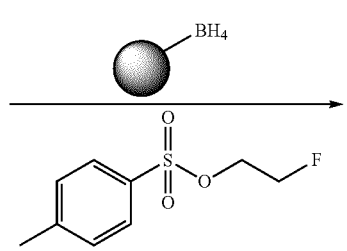

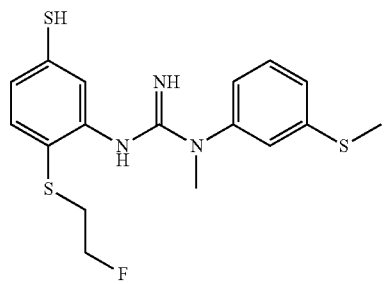

1,1'-(disulfanediylbis(2-chloro-5,1-phenylene))bis(3-methyl-3-(3-(methylthio)phenyl)guanidine) (0.15 g, 0.22 mmol), obtained as described in Example 1, and 2-fluoroethyl4-methylbenzenesulfonate (0.10 g, 0.45 mmol) was dissolved in ethanol (96%, 10 mL), and solid phase supported borohydride (0.45 g, ~1.11 mmol) was added. The resulting reaction suspension was heated under inert atmosphere to 60° C. for 17 hours. The suspension was filtered and the solid phase material was washed with ethanol (96%, 2*5 mL). The combined organic phases were concentrated under reduced pressure to give a moist crude that was redissolved in dichloromethane (10 mL), dried with magnesium sulfate (~0.3 g, 2.492 mmol), filtered and concentrated to dryness to give 3-(2-chloro-5-((2-fluoroethyl)thio)phenyl)-1-methyl-1-(3-(methylthio)phenyl)guanidine (0.13 g, 0.32 mmol, 70.7% yield) as a clear oil.

¹H NMR (400 MHz, CDCl₃): δ7.28-7.35 (m, 2H), δ7.05-7.25 (m, 4H), δ6.90-6.95 (dd, J₁=3.18 Hz, J₂=8.33 Hz 1H), δ4.6 (t, J=6.75 Hz, 1H), δ4.5 (t, J=6.75 Hz, 1H), δ3.9 (broad S, 1H), δ3.4 (s, 3H), δ3.2(t, J=6.75 Hz, 1H), δ3.15 (t, J=6.75 Hz, 1H), δ2.52 (S, 3H)δ1.65 (broad S, 1H).

What is claimed is:

1. A method to obtain a positron emission tomography (PET) tracer of Formula I:

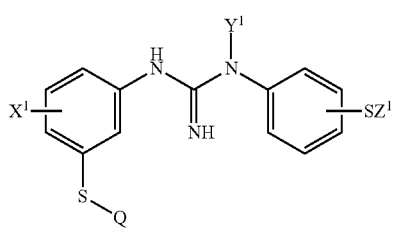

wherein:

X¹ is an X group selected from C₁₋₄ alkyl or halo;

Y¹ is a Y group selected from hydrogen or C₁₋₄ alkyl;

$Z^1$ is a Z group which is $C_{1-4}$ alkyl; and,

Q is $[^{11}C]C_{1-4}$ alkyl- or $[^{18}F]$—$C_{1-4}$fluoroalkyl-;

wherein said method comprises:

(a) providing a compound of Formula II:

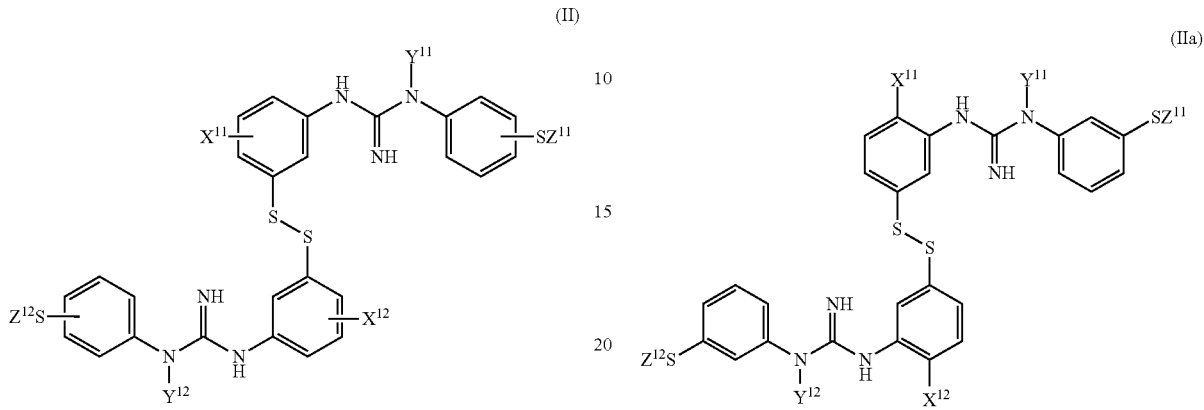

wherein:

$X^{11}$ and $X^{12}$ are the same and are both an X group as defined for $X^1$;

$Y^{11}$ and $Y^{12}$ are the same and are both a Y group as defined for $Y^1$; and, $Z^{11}$ and $Z^{12}$ are the same and are both a Z group as defined for $Z^1$;

(b) reducing said compound of Formula II with a reducing agent to obtain a compound of Formula III:

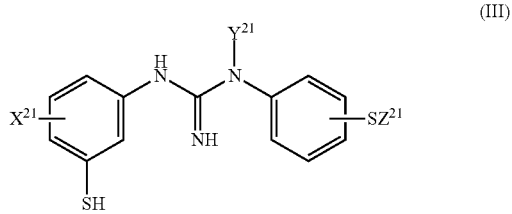

$X^{21}$ is an X group as defined for $X^1$;

$Y^{21}$ is a Y group as defined for $Y^1$; and, $Z^{21}$ is a Z group as defined for $Z^1$;

(c) reacting the compound of Formula III as obtained in step (b), with either $[^{11}C]C_{1-4}$ alkyl-$LG^1$ or $[^{18}F]$—$C_{1-4}$ fluoroalkyl-$LG^2$, wherein $LG^1$ and $LG^2$ are independently halo, or the group —O—$SO_2$—$R^1$ wherein $R^1$ represents an optionally-substituted $C_{6-10}$ aryl, an optionally-substituted $C_{1-4}$ alkyl, or $C_{1-4}$ fluoroalkyl, wherein said reacting is carried out in a suitable solvent.

2. The method as defined in claim 1 wherein said compound of Formula II is a compound of Formula IIa:

wherein:

$X^{11}$ and $X^{12}$ are the same and are both an X group as defined in claim 1;

$Y^{11}$ and $Y^{12}$ are the same and are both a Y group as defined in claim 1; and, $Z^{11}$ and $Z^{12}$ are the same and are both a Z group as defined in claim 1.

3. The method as defined in claim 1 wherein said X group is halo.

4. The method as defined in claim 1 wherein said Y group is $C_{1-4}$ alkyl.

5. The method as defined in claim 1 wherein said Z group is methyl.

6. The method as defined in claim 1 wherein said X group is chloro, said Y group is methyl and said Z group is methyl.

7. The method as defined in claim 1 wherein said reducing agent used in step (b) is selected from sodium borohydride ($NaBH_4$), zinc in hydrochloric acid, zinc in acetic acid, magnesium in hydrochloric acid, sodium hydrogentelluride (NaTeH) in ethanol, lithium aluminium hydride ($LiAlH_4$) in tetrahydrofuran, indium in ammonium chloride, and sodium hydride (NaH).

8. The method as defined in claim 1 wherein in said reacting step (c) the compound of Formula III is reacted with $[^{18}F]$—$C_{1-4}$ fluoroalkyl-$LG^2$.

9. The method as defined in claim 1 wherein said reducing step (b) and said reacting step (c) are carried out in immediate sequence.

10. The method as defined in claim 1 wherein said reducing step (b) and said reacting step (c) are carried out in the same vessel.

11. The method as defined in claim 1 wherein said method is automated.

12. A method for the preparation of the compound of Formula III as defined in claim 1, said method comprising reacting a compound of Formula IV:

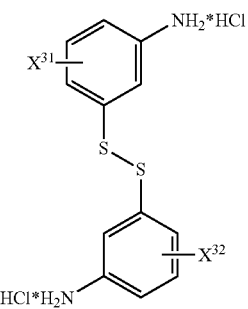

(IV)

wherein $X^{31}$ and $X^{32}$ are the same and are both an X group as defined in claim 1;
with a compound of Formula V:

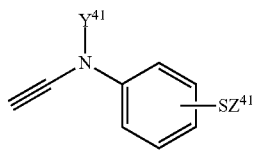

(V)

wherein $Y^{41}$ is a Y group as defined in claim 1, and $Z^{41}$ is a Z group as defined in claim 1;

to obtain a compound of Formula II as defined in claim 1; and, reducing said compound of Formula II using a reducing agent as defined in claim 1 to obtain said compound of Formula III.

13. A cassette for carrying out the method as defined in claim 11, wherein said cassette comprises:

(i) a vessel containing the compound of Formula II;

(ii) means for reacting said compound of Formula II with a reducing agent to form a compound of Formula III and, (iii) means for reacting said compound of Formula III with either [$^{11}$C]$C_{1-4}$ alkyl-$LG^1$ or [$^{18}$F]—$C_{1-4}$ fluoroalkyl-$LG^2$ to obtain a PET tracer of Formula I, wherein $LG^1$, $LG^2$, and said PET tracer of Formula I are as defined in claim 1.

14. The cassette as defined in claim 12 which further comprises:

(iv) an ion-exchange cartridge for removal of excess [$^{11}$C]$C_{1-4}$ alkyl-$LG^1$ or [$^{18}$F]-$C_{1-4}$ fluoroalkyl-LG2.

\* \* \* \* \*